(12) United States Patent
Lee

(10) Patent No.: US 8,359,693 B2
(45) Date of Patent: Jan. 29, 2013

(54) ELECTRIC BATTERY POWERED TOOTHBRUSH WITH INTEGRATED TONGUE CLEANER

(76) Inventor: Wang Ken Lee, Marietta, GA (US)

( * ) Notice: Subject to any disclaimer, the term of this patent is extended or adjusted under 35 U.S.C. 154(b) by 0 days.

(21) Appl. No.: 13/116,251

(22) Filed: May 26, 2011

(65) Prior Publication Data
US 2011/0289702 A1 Dec. 1, 2011

Related U.S. Application Data

(60) Provisional application No. 61/396,399, filed on May 27, 2010.

(51) Int. Cl.
A46B 13/02 (2006.01)
(52) U.S. Cl. .................... 15/22.1; 15/4; 15/28
(58) Field of Classification Search ............ 15/4, 22.1, 15/28
See application file for complete search history.

(56) References Cited

U.S. PATENT DOCUMENTS

| 2,215,031 | A | 9/1940 | Elmore |
| 5,226,197 | A | 7/1993 | Nack et al. |
| 5,709,004 | A | 1/1998 | Paduano et al. |
| 5,732,432 | A | 3/1998 | Hui |
| 5,987,681 | A | 11/1999 | Hahn et al. |
| 6,322,573 | B1 | 11/2001 | Murayama |
| 6,647,581 | B1 | 11/2003 | Persad et al. |
| 6,779,215 | B2 | 8/2004 | Hartman et al. |
| 7,430,777 | B2 | 10/2008 | Scherl |
| 7,962,988 | B2 * | 6/2011 | Sorrentino ............ 15/22.1 |
| 8,032,967 | B2 * | 10/2011 | Jimenez ............... 15/110 |
| 8,136,192 | B2 * | 3/2012 | Harrison et al. ........ 15/4 |

FOREIGN PATENT DOCUMENTS

GB 2237505 5/1991

* cited by examiner

*Primary Examiner* — Randall Chin
(74) *Attorney, Agent, or Firm* — Joel D. Myers; Myers & Associates, P.C.

(57) ABSTRACT

An oral care device includes an electrical toothbrush with integral tongue scrapers. The device includes an electrical tooth cleaning device and an electrical tongue cleaning device operated by a single motor. Cleaning gears disposed in a head portion of the device include both bristles for cleaning teeth and nodules for scraping the surface of the tongue. The bristles protrude from a first end of the cleaning gears and the nodules are formed on an opposite second end of the cleaning gears such that rotation of the cleaning gears provides movement of both the bristles and the nodules.

11 Claims, 9 Drawing Sheets

ELECTRIC BATTERY POWERED TOOTHBRUSH WITH INTEGRATED TONGUE CLEANER

FIELD OF THE INVENTION

The invention relates to an electric oral hygiene device for tongue and teeth cleaning.

BACKGROUND

Known electrical toothbrushes use electricity to drive either a motor or an electromagnetic oscillator to provide direct motion to the toothbrush bristles located on the toothbrush head, such as the disclosures in U.S. Pat. Nos. 2,215,031, 5,226,197, 5,709,004, 5,732,432, 5,987,681, 6,322,573, 6,647,581, 6,779,215, 7,430,777, and U.K. No. 2,237,505. These devices have dedicated bristle structures and mechanical motions to clean teeth, but most have no electrically driven specialized structures to clean the tongue.

Known tongue cleaners are predominately operated by hand. Because they are operated by hand, they have limited abilities compared to electrical models. There are also a few electrical tongue cleaners, but these have only the specialized ability to clean the tongue, therefore requiring a separate device to clean the teeth.

What is needed is a durable, effective and portable electrical hygiene device including both a tooth cleaning device and a tongue cleaning device.

SUMMARY

In accordance with the embodiments described herein, an oral care device comprises a head portion which includes a plurality of gear openings formed therein. A plurality of cleaning gears is respectively received in the gear openings. A bristle opening is formed in a first end portion of each cleaning gear and bristles protrude from each bristle opening for cleaning the teeth of the user. Further, a plurality of dynamic cleaning nodules is formed on a second end portion of each cleaning gear for cleaning a surface of the user's tongue. A motor drives the cleaning gears, thereby causing movement of the bristles and the dynamic cleaning nodules.

The head portion has a first side surface and a second side surface opposite the first side surface such that the bristles protrude from the first side surface of the head portion and the dynamic cleaning nodules protrude from the second side surface of the head portion.

BRIEF DESCRIPTION OF THE DRAWINGS

Features, aspects, and advantages of the embodiments described herein will become better understood with regard to the following description, appended claims, and accompanying drawings.

Figure 1:
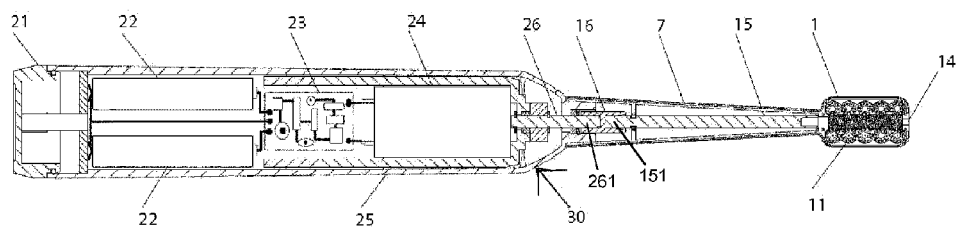
FIG. 1 is a side cutaway view of an embodiment of the oral hygiene device described herein.
Figure 2:
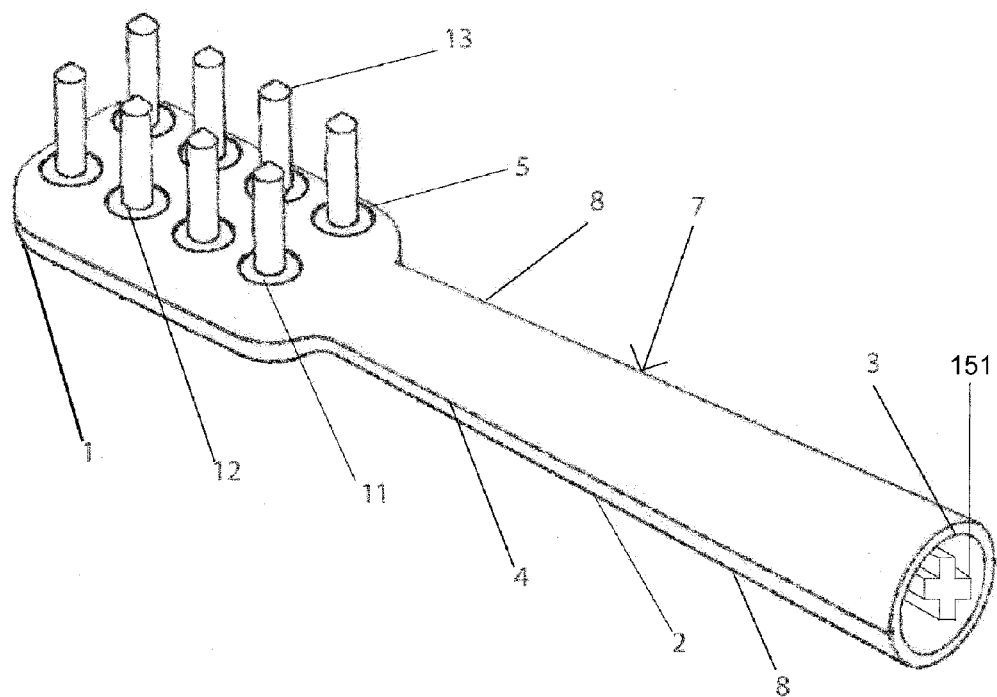
FIG. 2 is a perspective view of the oral hygiene attachment of FIG. 1.
Figure 3:
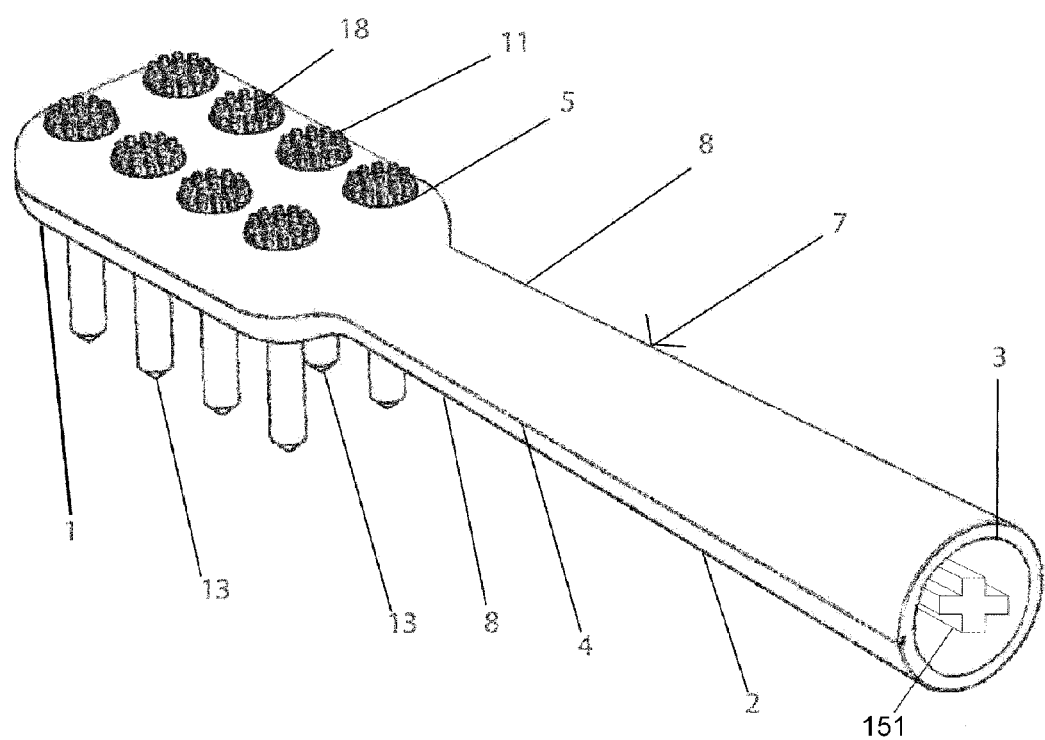
FIG. 3 is a perspective view of the oral hygiene attachment of FIG. 1.
Figure 4:
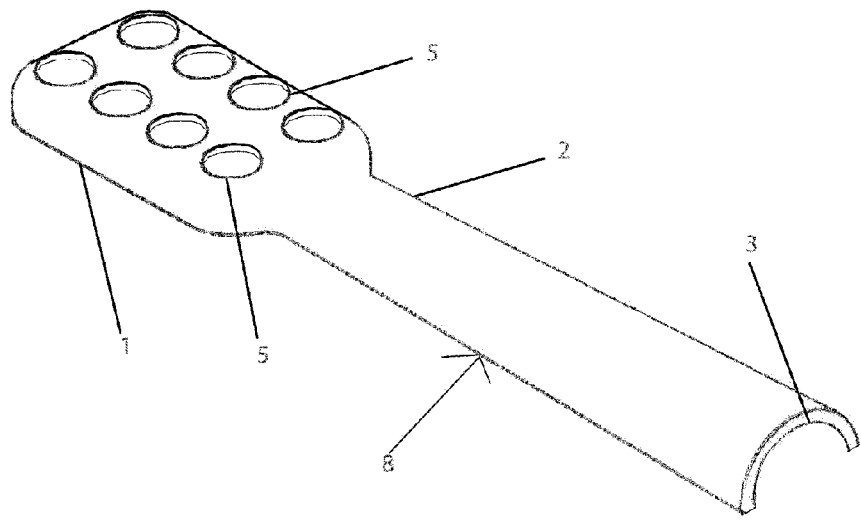
FIG. 4 is a perspective view of the encasement of FIG. 2.
Figure 5:
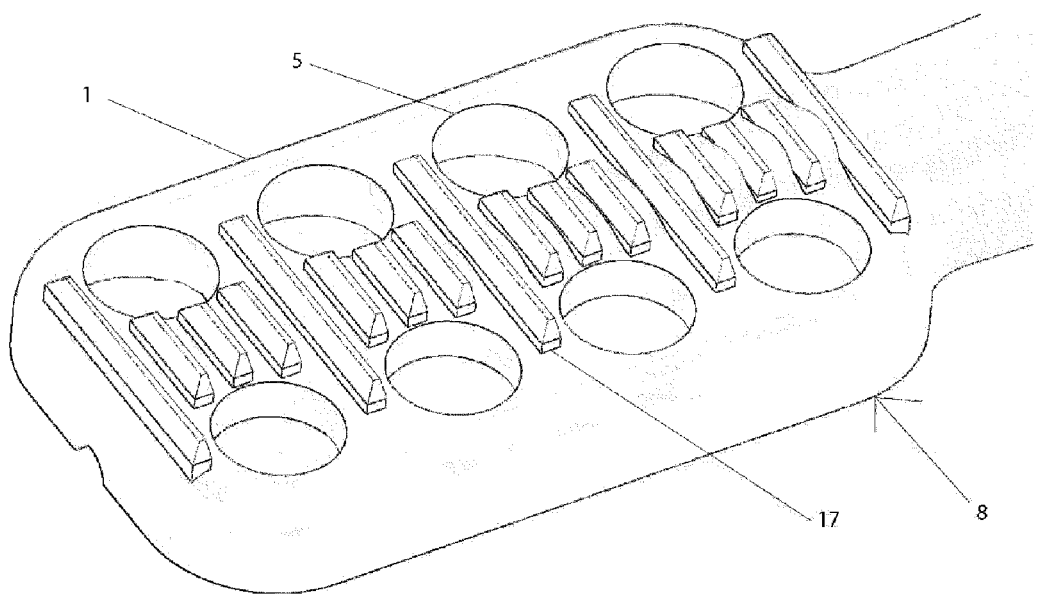
FIG. 5 is a perspective view of the head of FIG. 2.

It should be noted that the drawing figures are not necessarily drawn to scale, but instead are drawn to provide a better understanding of the components thereof, and are not intended to be limiting in scope, but rather to provide exemplary illustrations.

DETAILED DESCRIPTION OF VARIOUS EMBODIMENTS

Referring to the drawings, FIG. 1 shows an electric toothbrush and tongue cleaner 30, which includes a toothbrush attachment section 7 connected to a body 25 which is sealed by a battery cap 21. The attachment section 7 includes a head 1. The head 1 has cleaning gears 11 disposed therein that are driven by a worm gear 14 which is interference fitted to a drive shaft 15. The drive shaft 15 is connected to a motor drive shaft 26 via a coupling 16. The motor drive shaft 26 is driven by a motor 24. The motor 24 is controlled by a circuit board 23 and powered by batteries 22.

Still referring to FIG. 1, the batteries 22 are sealed from the external environment by the battery cap 21 and the body 25. The circuit board 23 controls the direction and duration of the motor 24, which in turn drives the motor drive shaft 26 which transmits the power to the drive shaft 15 via the coupling 16. The drive shaft 15 then turns the worm gear 14 which transmits power to the cleaning gears 11 located in the head 1.

The batteries 22 can be any sized cell battery such as lithium ion, lithium, nickel metal hydride, lead acid, or alkaline batteries. The motor 24 can be any small direct current motor. The circuit board 23 is preferably a low power-consuming circuit board that is waterproof. The housing comprises the body 25, the toothbrush attachment 7, and the cap 21. These pieces can be made of plastic, metal, or any other material that can be formed into the shapes of these pieces. The mechanical elements of the device include the motor drive shaft 26, the coupling 16, the drive shaft 15, the worm gear 14, and the cleaning gears 11. These members can be made of any suitable material that can withstand the mechanical forces and environmental conditions of the device. For example, the cleaning gear 11 can be made of copolymer plastic, polyethylene, or Teflon infused ABS, while the worm gear 14 and the motor drive shaft 26 can be made of bronze, stainless steel, aluminum or plastic, and the drive shaft 15 can be molded of an inexpensive plastic material.

Referring to FIGS. 2 to 5, there is shown a toothbrush attachment 7 that consists of head 1 and neck 2 portions. At the bottom of the neck 2 portion there is an attachment opening 3 for connecting to the body 25. Two encasements 8, top and bottom, that can be identical in shape or asymmetrical are connected at the seam 4 to form the complete toothbrush attachment 7. Gear openings 5 are respectively formed in the top and bottom encasements 8 in the head portion of the toothbrush attachment 7 for accommodating the cleaning gears 11. Bristles 13 protrude from bristle openings 12 formed in the cleaning gears 11 and extend through the gear openings 5 in the top encasement 8. Dynamic cleaning nodules 18 are formed on or attached to the cleaning gears 11 and protrude through the gear openings 5 in the bottom encasement 8. Static cleaning nodules 17 can also be formed in the head 1 on the bottom encasement 8.

The bristles 13 are used to clean the teeth and the cleaning nodules 18 are used to clean the tongue. The bristles 13 can be a combination of slender shaped filaments for flossing between teeth or densely packed bristles for polishing the surface of the teeth or gum massaging. The neck 2 is an extension for allowing easy access to the deeper portions of the mouth. The gear openings 5 in the top and bottom encasements 8 support and guide the rotating cleaning gears 11.

The seam 4 of the toothbrush attachment 7 can be connected by heat welding, screws, ultrasonic welding, interlocking edge mechanism or other suitable methods. The dynamic cleaning nodules 18 have a rounded shape, but could also have a cross shape, a triangle shape, or any other geometric configuration suitable for cleaning the surface of the tongue. The static cleaning nodules 17 are used for manually scrubbing the tongue.

All parts of the device can be plastic injection molded, excluding the bristles 13, but can also be made of metal or other suitable materials. The bristles 13 can also be made of plastic or any other material that is suitable for cleaning between teeth and gum areas. The cleaning gear 11 can be made of copolymer plastic or metal with a low coefficient of friction while the encasement 8 can be constructed of most injection moldable plastics.

Figure 6A:
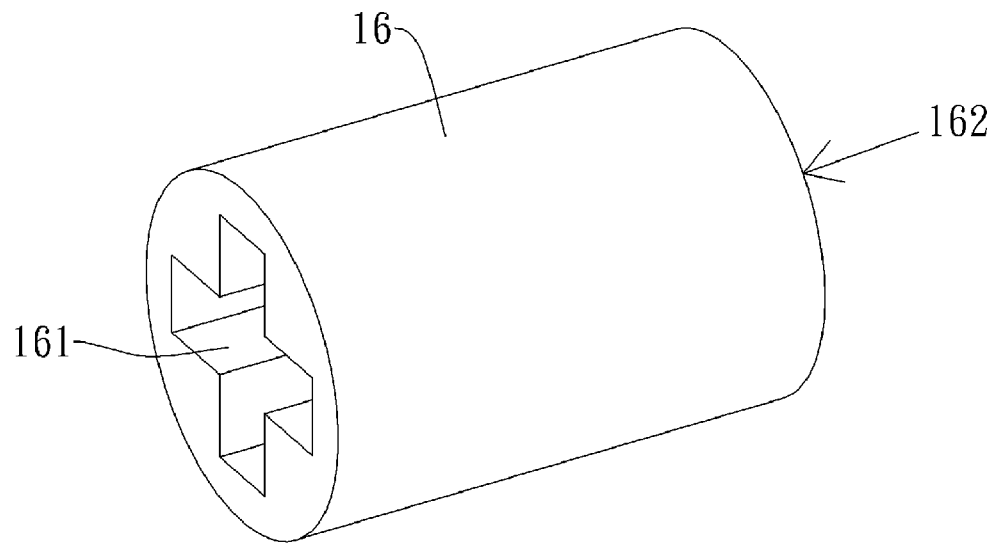
FIG. 6A is a perspective view of the coupling of FIG. 1.
Figure 6B:
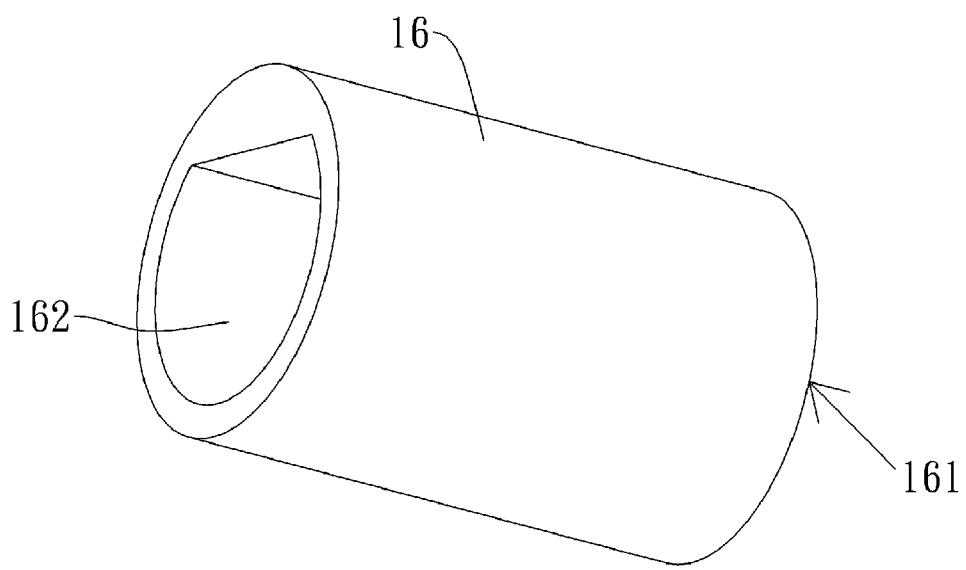
FIG. 6B is another perspective view of the coupling of FIG. 1.

Referring now to FIGS. 6A and 6B, there is a coupling 16 which is used to connect the worm gear 14 to the drive shaft 15, or the drive shaft 15 to the motor drive shaft 26. The drive shaft 15, shown in FIG. 3, has a cross shaped head enabling a loose fit coupling with the coupling 16.

As shown in FIGS. 6A and 6B, the coupling 16 has two openings. A D-shaped opening 162 is formed at a first end of the coupling 16 for receiving a D-shaped member 261 formed on the motor drive shaft 26. A cross-shaped opening 161 is formed at a second end of the coupling for receiving a cross-shaped member 151 formed on the drive shaft 15. The cross-shaped opening 161 is a loose fitting asymmetric connection point that facilitates easy disassembly of the drive shaft 15. The coupling 16 can made of plastic and any other suitable material. The asymmetric connection could also have a star shape.

Figure 7:
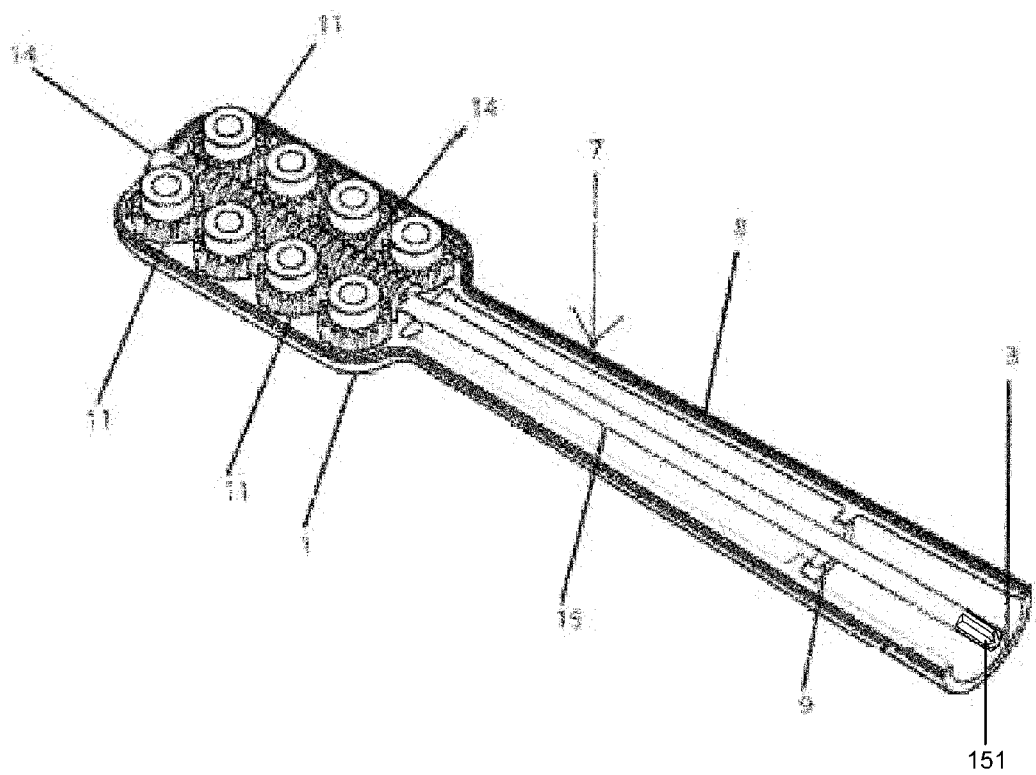
FIG. 7 is a perspective view of the oral hygiene attachment of FIG. 2.
Figure 8:
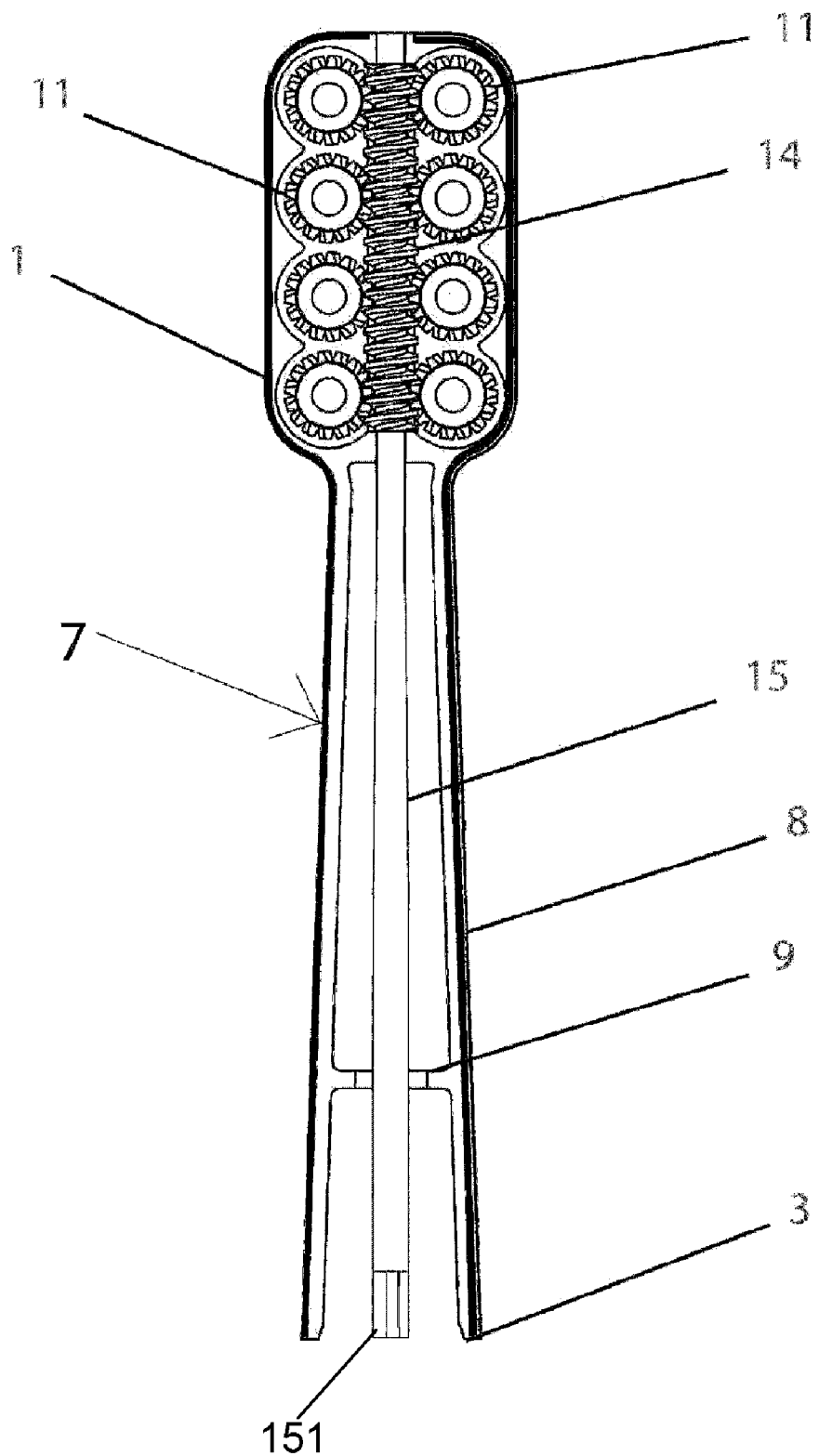
FIG. 8 is a top view of the oral hygiene attachment of FIG. 2.

Referring now to FIGS. 7 and 8, the top and bottom encasements 8 hold the cleaning gears 11 in place. The cleaning gears 11 are driven by the worm gear 14. The worm gear 14 can be attached directly to the drive shaft 15 by interference fit as shown in FIG. 1 or by a coupling 16. The drive shaft 15 is supported by the positioned opening 9 while not engaged with the motor drive shaft 26. The coupling 16 is engaged with the D-shaped member 261 of the motor drive shaft 26.

The drive shaft 15 is connected to the electric motor 24 by the coupling 16. The drive shaft 15 torque is transmitted to the worm gear 14 by an interference fit, which in turn drives the cleaning gears 11 causing the cleaning gears to spin. The top and bottom encasements 8 hold all of the parts together and shield the parts from external elements, such as water.

Figure 9:
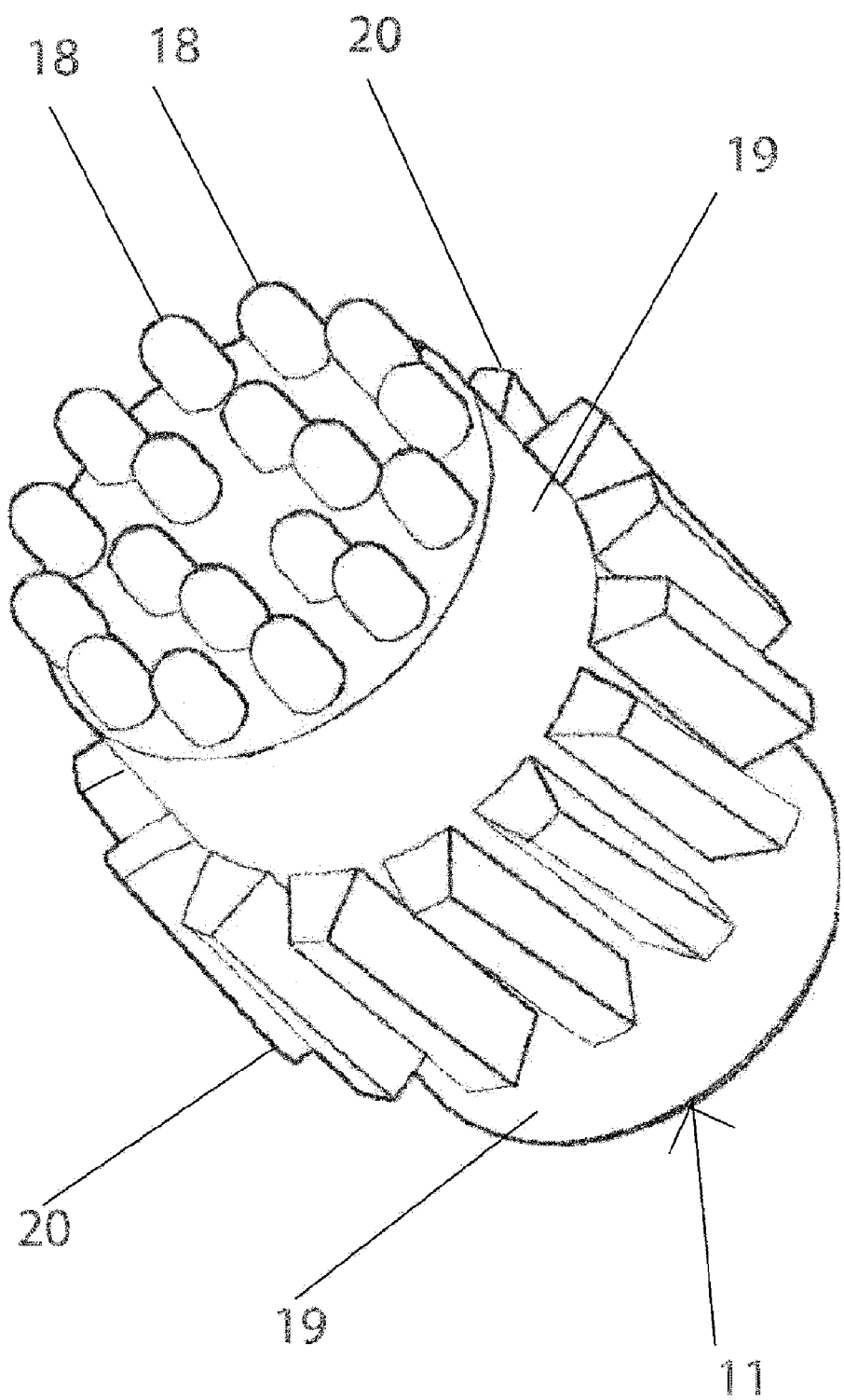
FIG. 9 is a top perspective view of the cleaning gear of FIG. 1.
Figure 10:
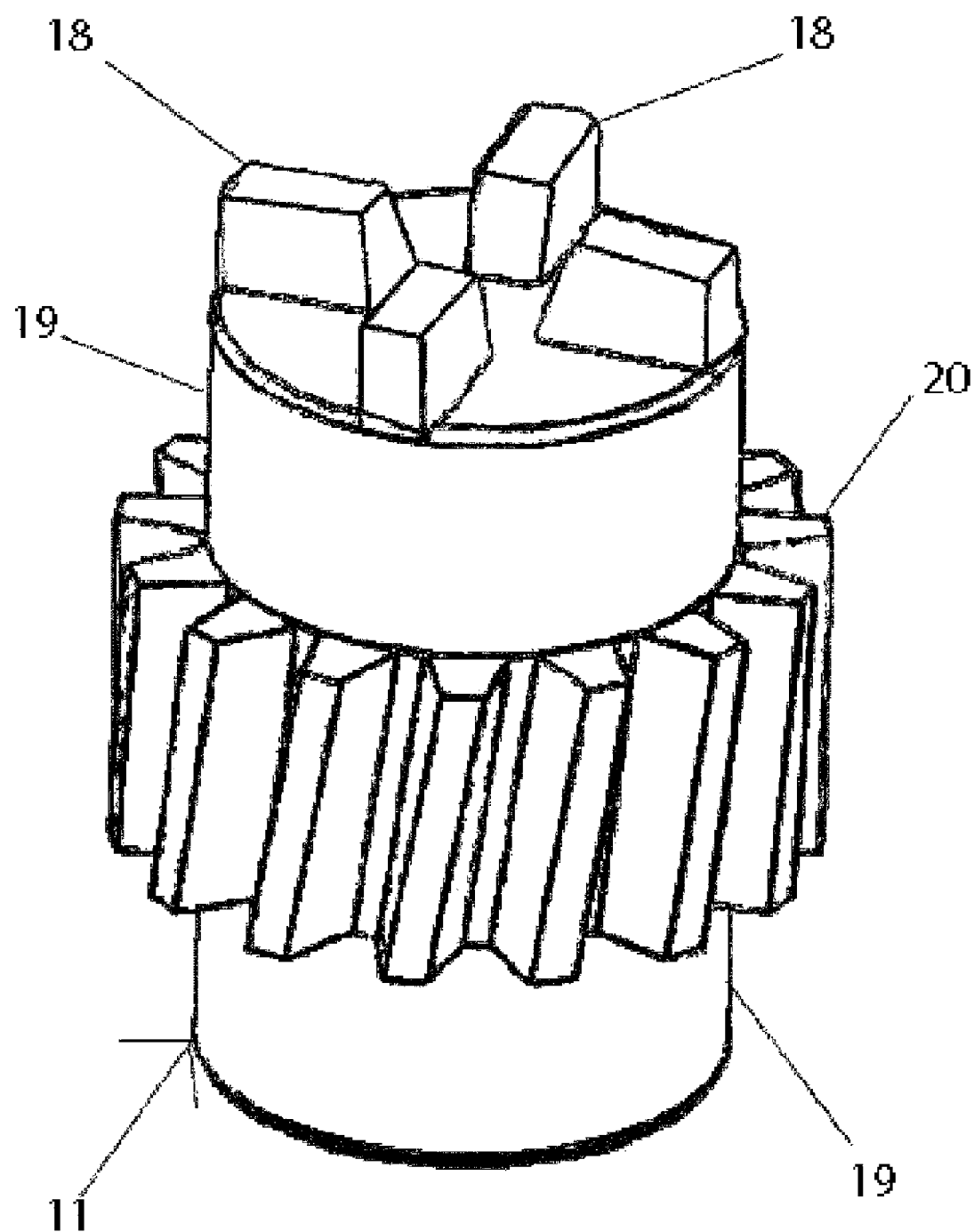
FIG. 10 is an alternate top perspective view of the cleaning gear of FIG. 1.
Figure 11:
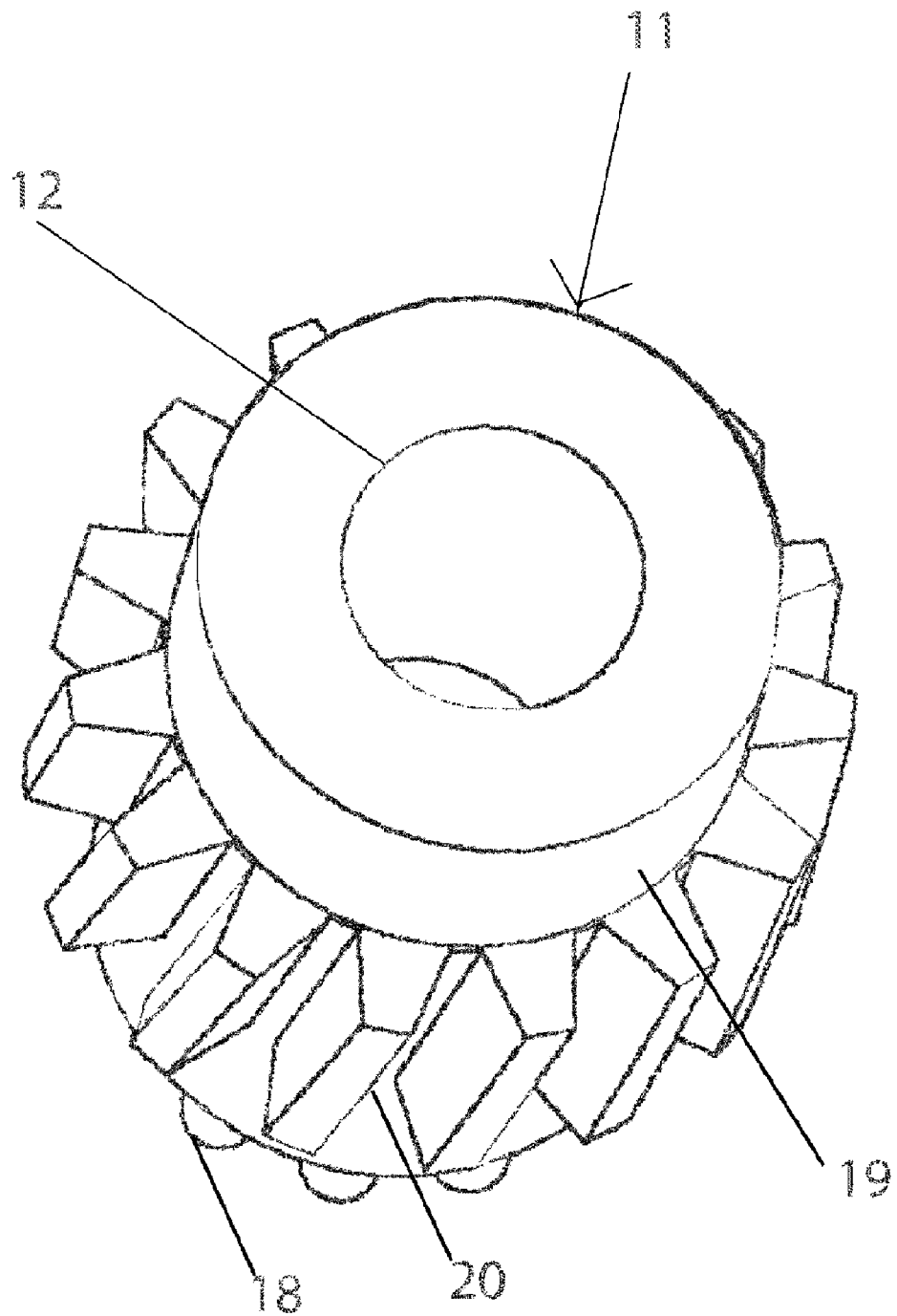
FIG. 11 is a bottom perspective view of the cleaning gear of FIG. 1.

A plurality of teeth 20 are formed along the sides of the cleaning gears 11, as shown in FIGS. 9 to 11. Two rotating surfaces 19 are also respectively formed above and below the teeth 20. The cleaning nodules 18 are located on a bottom face of the cleaning gears 11 while the bristle opening 12 is located on an opposing top face.

The teeth 20 of the cleaning gear 11 are driven by the worm gear 14. The two rotating surfaces 19 of the cleaning gear are held in place by the gear openings 5 formed in the top and bottom encasements 8. The bristle opening 12 holds the bristles 13 which are used for cleaning teeth. The cleaning nodules 18 formed on the bottom face of the cleaning gears 11 are used for cleaning the tongue. The cleaning gear 11 can be made of metal or injection molded plastic.

The embodiments described herein are useful for travel since they are portable, save energy, and are separable into a head portion 1 and a body 25 portion for ease of storage. The device is less prone to breakage due to the minimal number of parts and the absence of any speed reduction devices coupling the motor 24 and worm gear 14. The non reciprocal/oscillating motion of the bristle and tongue scraper enable the toothbrush and tongue cleaner to operate with minimal battery power consumption, and minimal noise and vibration, making it more comfortable for users that are more sensitive to noise and vibration.

The integrated tongue scraper has an innovative feature that allows the cleaning of the tongue by both dynamic and static scrapers. The rotating motion of the tongue cleaning nodules 18 allows for minimal motion of the actual toothbrush while enabling enhanced cleaning of the tongue's surface because the rotating tongue scrapers are moving continuously.

The attachment head 1 can be changed for other types of heads such as tooth massaging devices or flossing devices. The coupling 16 allows for increased efficiency of energy transfer and less susceptibility to misalignment of rotating shafts. The coupling 16 transfers torque while minimizing misalignment of radial and axial loads. The power source can be a disposable battery, rechargeable battery, a USB cable, a proprietary charger for rechargeable batteries, or other recharging devices such as solar energy or a hand crank generator. There can be an optional circuit which alternates between clockwise and counterclockwise motor rotation every 30 seconds to allow for a more even and thorough cleaning of the mouth and tongue surfaces.

Although this invention has been disclosed in the context of certain exemplary embodiments and variations thereof, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. An oral care device, comprising:
a head portion including a plurality of gear openings formed therein;
a plurality of cleaning gears respectively received in the gear openings; a bristle opening formed in a first end portion of each cleaning gear; bristles protruding from each bristle opening for cleaning teeth; a plurality of dynamic cleaning nodules formed on a second end portion of each cleaning gear for cleaning a surface of the tongue;
a motor for driving the cleaning gears, thereby causing movement of the bristles and the dynamic cleaning nodules.

2. The oral care device of claim 1, wherein the head portion has a first side surface and a second side surface opposite the first side surface, and the bristles protrude from the first side surface of the head portion and the dynamic cleaning nodules protrude from the second side surface of the head portion.

3. The oral care device of claim 1, wherein static cleaning nodules are formed on the second side surface of the head portion for cleaning the surface of the tongue.

4. The oral care device of claim 1, further comprising a worm gear coupled to the motor and engaging the cleaning gears for transferring motion from the motor to the cleaning gears.

5. The oral care device of claim 4, further comprising:
a drive shaft connected to the worm gear;
a motor drive shaft connected to the motor;
a coupling having a first end portion connected to the motor drive shaft and a second end portion connected to the drive shaft,
wherein at least one of the first end portion and the second end portion has one of a D-shaped opening and a cross-shaped opening.

6. The oral care device of claim 5, wherein at least one of the motor drive shaft and the drive shaft has one of a D-shaped member and a cross-shaped member formed thereon for engaging with the D-shaped opening or the cross-shaped opening.

7. The oral care device of claim 1, further comprising:
a body which includes the motor;
an attachment portion which includes the head portion and a neck portion extending from the head portion, the drive shaft being disposed in the neck portion,
wherein the attachment portion is detachably connected to the body.

8. The oral care device of claim 7, wherein the motor drive shaft protrudes from the body for engaging with the attachment portion via the coupling.

9. The oral care device of claim 7, wherein the body includes a battery chamber and a battery cap for covering the battery chamber.

10. The oral care device of claim 1, wherein the cleaning gears each include a plurality of gear teeth and first and second rotating surfaces disposed on opposite sides of the gear teeth.

11. The oral care device of claim 10, further comprising a worm gear coupled to the motor and engaging the gear teeth of the cleaning gears for transferring motion from the motor to the cleaning gears.

* * * * *